United States Patent [19]

Chavdarian

[11] Patent Number: 4,837,209
[45] Date of Patent: Jun. 6, 1989

[54] S-CYCLOALKYLMETHYL TRITHIOPHOSPHONATE INSECTICIDES

[75] Inventor: Charles G. Chavdarian, Martinez, Calif.

[73] Assignee: Stauffer Chemical Company, Westport, Conn.

[21] Appl. No.: 69,996

[22] Filed: Jul. 6, 1987

[51] Int. Cl.⁴ .................... A01N 57/04; C07F 9/32
[52] U.S. Cl. .................................... 514/141; 558/214
[58] Field of Search .................... 558/214; 514/141

[56] References Cited

U.S. PATENT DOCUMENTS

| | | | |
|---|---|---|---|
| 3,514,504 | 5/1970 | Peterson | 558/214 |
| 4,258,038 | 3/1981 | Strong | 558/214 |
| 4,565,809 | 1/1986 | Chavdarian et al. | 514/112 |

FOREIGN PATENT DOCUMENTS 210608 2/1987 European Pat. Off. .
1139492 11/1962 Fed. Rep. of Germany .

Primary Examiner—Anton H. Sutto
Attorney, Agent, or Firm—Joel G. Ackerman

[57] ABSTRACT

Compounds and compositions containing them, for insecticidal control, particularly for use as soil and/or foliar insecticides, have the formula

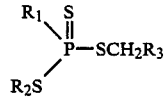

in which
$R_1$ is methyl or ethyl;
$R_2$ is $C_1$–$C_6$ alkyl; and
$R_3$ is $C_3$–$C_6$ cycloakyl.

7 Claims, No Drawings

S-CYCLOALKYLMETHYL TRITHIOPHOSPHONATE INSECTICIDES

SUMMARY OF THE INVENTION

This invention relates to a series of trithiophosphonate insecticides having the formula

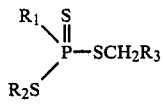

in which
$R_1$ is methyl or ethyl;
$R_2$ is $C_1$–$C_6$ alkyl; and
$R_3$ is $C_3$–$C_6$ cycloalkyl; together with insecticidal compositions containing such compounds, and methods for controlling insects.

The term "alkyl" refers to saturated acyclic hydrocarbyl groups having from 1 to 6 carbon atoms, such as methyl, ethyl, and the various propyl, butyl, amyl and hexyl groups. Preferably $R_2$ is $C_1$–$C_4$ alkyl. More preferably, $R_2$ is a $C_3$–$C_6$ alpha-branched alkyl group such as isopropyl, sec-butyl or tert-butyl. Most preferably $R_2$ is an alpha,alpha-doubly branched alkyl group such as tertiary butyl.

The term "cycloalkyl" refers to saturated cyclic hydrocarbyl groups and includes cyclopropyl, cyclobutyl, cyclopentyl and cyclohexyl. Of these, cyclopropyl is most preferred.

The term "insects" as used herein refer to the broad and commonly understood usage rather than to those creatures which in the strict biological sense are classified as insects, and includes, in addition to those belonging to the insecta, some classes of acarids such as spiders, mites, ticks, and the like, particularly mites.

The compounds of the present invention may be prepared by a two-step process.

In the first step the appropriate alkyl thionophosphine sulfide is reacted with two equivalents of a desired mercaptan in the presence of a base to produce a thioic acid salt, according to the equation:

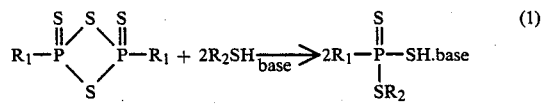

In the second step, the thioic acid salt is reacted with an appropriate cycloalkylmethyl halide:

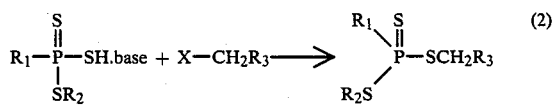

in which $R_1$–$R_3$ are as previously defined and X stands for halogen, preferably chloro or bromo.

The starting material sulfides for Reaction 1 may be obtained for instance by the procedure described in P.E. Newallis et al., *Journal of Organic Chemistry*, 1962, Vol. 27, p. 3829.

Reaction 1 is advantageously carried out at a temperature of from about −40° C. to about 150° C., preferably from about 0 to about 70° C., in an organic solvent in the presence of a base, preferably a tertiary amine. Suitable solvents include aromatic hydrocarbons such as benzene or toluene, ethers such as diethyl ether or tetrahydrofuran, and ketones such as acetone. Suitable tertiary amines include triethylamine, dimethylaniline, diethylaniline, and pyridine. Inorganic bases such as sodium hydroxide could be used in this step, but are less desirable as the resulting salts are less soluble in the solvents utilized. As the reaction is exothermic, the base is preferably added dropwise when operating on the laboratory scale. The product may be recovered by evaporating or distilling off the solvent.

Reaction 2 is conducted in an organic solvent such as that utilized in the first reaction, at a temperature of from about 20° C. to about 130° C., preferably from about 20 to about 70° C. The cycloalkylmethyl halide may be either a chloride or bromide. The product may be recovered by removing the precipitated salt, followed by evaporating or distilling off the solvent, and purification by either chromatography or distillation.

The following represent an example of the preparation of a compound of this invention.

EXAMPLE 1

Preparation of S-t-Butyl S-cyclopropylmethyl methylphosphonotrithioate (a). To a slurry of 20.05 grams (g) (0.091 mole) of methylthionophosphine sulfide in 125 milliliters (ml) of tetrahydrofuran (under nitrogen) was added 21.5 ml (17.18 g, 0.191 mole) of 2-methyl-2-propanethiol. To the solution was added 26.6 ml (19.3 ml, 0.191 mole) of triethylamine, dropwise. The mixture was then refluxed for 4 hours, cooled, and evaporated to give 53.89 g (98% of theoretical yield) of a white, crystalline solid, the triethylamine salt of S-t-butyl methylphosphonotrithioic acid.

(b). To a solution of 2.5 g (0.0083 mole) of the triethylamine salt obtained in step (a) in 25 ml of tetrahydrofuran (under nitrogen) was added a solution of 1.12 g (0.0083 mole) of cyclopropylmethyl bromide in 5 ml of tetrahydrofuran. The solution was refluxed for 6 hours. The resultant white, solid precipitate was removed by filtration. To the solution was added 10 ml of water; then the mixture was extracted with ether (2 × 10 ml). The ethereal layer was washed with saturated aqueous sodium chloride, dried with magnesium sulfate, and evaporated to produce an oil. Purification by a preparative, centrifugally-accelerated, thin-layer (4 mm, silica gel) chromatograph (with 95:5 hexane-acetone as eluent) afforded 1.29 g (61% of theoretical yield) of the title compound, a clear, colorless, mobile oil. The structure was confirmed by nuclear magnetic resonance, infrared and mass spectroscopy.

Insecticidal Evaluation Tests

The compound of Example 1 above was tested for insecticidal activity using the following testing procedures. LD-50 values, based on the results of these tests, and/or calculated according to dosage-mortality curves, are expressed in Table I.

Housefly [*Musca domestica*]:

The test compound was diluted in acetone and aliquots pipetted onto the bottom of aluminum dishes. To ensure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1–2 days old. The cages were covered on the bottom with cellophane and on the top with tulle netting, and each contained a sugar-water saturated cotton plug for maintenance of the flies. Mortality was recorded after 48 hours. Test levels ranged from 100 ug/25 female houseflies downward. The LD-50 value is expressed below in Table II under the heading "HF", in terms of ug of the test compound per 25 female flies.

Black Bean Aphid [*Aphis fabae (Scop.)*]:

Nasturtium plants (Tropaeolum sp.) approximately 5 cm tall, were transplanted into sandy loam soil in small cups and infested with 25-50 black beam aphids of mixed ages. Twenty-four hours later they were sprayed to the point of runoff with 50-50 acetone-water solutions of the test compound. Treated plants were held in the greenhouse and mortality was recorded after 48 hours. Test concentrations ranged from 0.05% downward. The LD-50 value is expressed below in Table II under the heading "BA" in terms of percent of the test compound in the sprayed solution.

Tobacco Budworm [*Heliothis virescens* (Fabricius)]:

(a) Contact: The test compound was diluted in a 50—50 acetone-water solution. Cotton (Gossypium sp.) cotyaledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 0.1% downward. The LD-50 value is expressed below in Table II under the heading "TBW-C" in terms of percent of the test compound in the solution.

(b). Eggs. Paper towel patches of 2-day old eggs of the tobacco budworm were dipped in acetone solutions of the test compound and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LD-50 value is expressed below in Table II under the heading "TBW-E" in terms of percent of the test compound in the solution.

Beet Armyworm (*Spodoptera exigua*):

The test compound was diluted in a 50—50 acetone-water solution. Young leaves of sugar beets (*Beta vulgaris*) were immersed in the test solutions for 2-3 seconds and placed on a wire screen to dry. The dried leaves were placed in petri dishes containing a moistened filter paper and infested with five second-instar beet armyworm larvae. The dishes were placed in a high humidity chamber. Mortality of the larvae was recorded five days later. Test concentrations ranged from 0.1% downward. The LD-50 value is expressed below in Table II under the heading "BAW" in terms of percent of the test compound in solution.

Cabbage Looper [*Trichoplusia ni* (Hubner)]:

The test compound was diluted in a 50—50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 5 days later. Test concentrations ranged from 0.1% downward. The LD-50 value is expressed below in Table II under the heading "CL" in terms of percent of the test compound in solution.

Western Spotted Cucumber Beetle Larvae [*Diabrotica undecimpunctata undecimpunctata* (Mannherheim)]:

Ten grams of moist potting soil was placed in a plastic cup. The test compound was dissolved in acetone. A 0.05 ml aliquot of the test sample, diluted to the desired concentration, was added to the soil. The cup was capped and the soil was mixed on a vortex mixer for approximately 15 seconds. An indentation was made on the surface of the soil and approximately 50 Diabrotica eggs were added. The eggs were covered with soil and maintained at room temperature (approximately 70° F. or 21° C.). Four days later a section of Romaine lettuce (*Latuca sativa*) leaf was placed in the treated cups. One week later the cups were examined for live larvae. Test concentrations ranged from 25 ppm downward. The LD-50 value is expressed below in Table II under the heading "Diabrotica" in terms of ppm of the test compound in the soil.

Acaricidal Evaluation Test

The two-spotted mite (2SM) [*Tetranychus urticae* (Koch)] was employed in tests for miticides. The test procedure was as follows:

Pinto bean plants (Phaseolus sp.) approximately 10 cm tall, were transplanted into sandy loam soil in small cups and thoroughly infested with two-spotted mites of mixed ages and sexes. Twenty-four hours later the infested plants were inverted and dipped for 2-3 seconds in 50—50 acetone-water solutions of the test compound. Treated plants were held in the greenhouse, and 7 days later mortality was determined for both adult mites and the nymphs hatching from eggs which were on the plants at the time of treatment. Test concentrations ranged from 0.05% downward. The LD-50 value is expressed below in Table II under the headings "2SM-A" (i.e., adults) and "2SM-E" (i.e. eggs) in terms of percent concentration of the test compound in the solution.

Aster Leafhopper [*Macrosteles fascifrona* (Stal)]:

Oat seedlings (Avena sp.) were grown in a commercial potting soil in plastic cups. When the plants were approximately 10 cm tall they were thinned to 3 plants per cup and dipped for 2-3 seconds in 50—50 acetone-water solutions of the test compound. When the plants had dried, a clear plastic tube was placed over them and the bottom end pressed into the cup. Ten aster leafhopper adults/numphs were then placed in each tube and the tops of the tubes covered with white organdy cloth. Mortality counts were made after 48 hours. Test concentrations ranged from 0.05% downward. The LD-50 value is expressed below in Table II under the heading "LH" in terms of percent of the test compound in the solution.

TABLE I

| Cmpd. No. | HF ug | BA, % | 2-SM A, % | 2-SM E, % | (LD$_{50}$) TBW, % C | (LD$_{50}$) TBW, % E | BAW, % | CL, % | LH, % | Diabrotica, ppm (soil) |
|---|---|---|---|---|---|---|---|---|---|---|
| 1 | 33 | 0.001 | 0.006 | <0.05 | 0.007 | 0.001 | 0.01 | 0.002 | 0.01 | 0.3 |

Soil Residual Control of Diabrotica

The test compound was incorporated into 200 g of soil at a concentration of 2 ppm in the soil. The soil was maintained at a constant soil moisture in a closed container at 80° F. (27° C.). At weekly intervals, the soil was shaken and 10-gram samples were taken and placed in a small cup. An indentation was made on the soil surface and approximately 50 Diabrotica eggs were added, covered with soil, and the cup covered. A piece of Romaine lettuce was added four days later. The cups were examined for live larvae one week later.

At the concentration of 2 ppm, the test compound exhibited 14 weeks of control (100% mortality of Diabrotica).

In practice, a pure compound can be used as an insecticide. However, in general, the compound is first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein.

Solid carriers or diluents included in such compositions or formulations may include, for example, ground natural minerals such as kaolins, alumina, calcium carbonate, silica, kieselguhr, clays, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of akali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1–50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 112kg/ha).

It should be noted that the active compound need not be insecticidally active per se to effect insect control. The purposes of this invention are fully serves if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplane as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

|  | Weight % |
|---|---|
| Composition A: Wettable Powder Component | |
| Compound 1 | 80 |
| wetting agent (sodium dialkyl-naphthalene sulfonate) | 1 |
| dispersing agent (sodium lignosulfonate) | 4 |
| diluent (aluminum magnesium silicate) | 15 |
| Total | 100% |
| Composition B: Granular Solid Component | |
| Compound 1 | 10 |
| calcined diatomaceous earth granules | 85 |
| triethylene glycol | 5 |
| Total | 100% |
| Composition C: Dilute Solution Component | |
| Compound 1 | 5 |
| solvent (xylene) | 95 |
| Total | 100% |
| Composition D: Emulsifiable Concentrate Component | |
| Compound 1 | 50 |
| Emulsifier (blend of metal sulfonates and polyoxyethylene ethers) | 10 |
| solvent (xylene) | 40 |
| Total | 100% |
| Composition E: Concentrated Solution Component | |
| Compound 1 | 90 |
| solvent (xylene) | 10 |
| Total | 100% |

What is claimed is:

1. A method for inhibiting or controlling insects comprising applying to an insect, the locus of an insect, or a locus at which insecticidal control is desired, an insecticidally effective amount of a compound having the formula

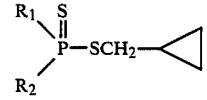

in which $R_1$ is methyl or ethyl and $R_2$ is $C_1$–$C_6$ alkyl.

2. A method according to claim 1 in which the insect to be inhibited or controlled is a soil-dwelling insect.

3. A method according to claim 1 in which the insect to be controlled or inhibited is of the genus Diabrotica.

4. A compound having the formula

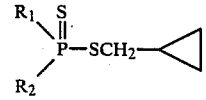

in which $R_1$ is methyl or ethyl and $R_2$ is $C_1$–$C_6$ alkyl.

5. A compound according to claim 4 in which $R_2$ is $C_3$–$C_6$ alkyl.

6. A compound according to claim 4 in which $R_2$ is an alpha, alpha-doubly branched $C_3$–$C_6$ alkyl.

7. An insecticidal composition comprising
(a) an insecticidally effective amount of a compound as defined in claim 4; and
(b) an insecticidally suitable inert diluent or carrier.

* * * * *